(12) United States Patent
Hauck et al.

(10) Patent No.: US 10,585,066 B2
(45) Date of Patent: Mar. 10, 2020

(54) HIGH ACCURACY ION MOBILITY SPECTROMETRY

(71) Applicant: Washington State University, Pullman, WA (US)

(72) Inventors: Brian Hauck, Rosedale, MD (US); William Siems, Spokane, WA (US); Vincent McHugh, White Hall, MD (US); Charles S. Harden, Bel Air, MD (US); Herbert H. Hill, Jr., Pullman, WA (US)

(73) Assignee: Washington State University, Pullman, WA (US)

( * ) Notice: Subject to any disclaimer, the term of this patent is extended or adjusted under 35 U.S.C. 154(b) by 0 days.

(21) Appl. No.: 16/005,337

(22) Filed: Jun. 11, 2018

(65) Prior Publication Data

US 2018/0372683 A1 Dec. 27, 2018

Related U.S. Application Data

(60) Provisional application No. 62/518,098, filed on Jun. 12, 2017.

(51) Int. Cl.
*G01N 27/62* (2006.01)
*H01J 49/24* (2006.01)
*H01J 49/14* (2006.01)
*H01J 49/42* (2006.01)
*H01J 49/40* (2006.01)

(52) U.S. Cl.
CPC ........... *G01N 27/622* (2013.01); *H01J 49/14* (2013.01); *H01J 49/24* (2013.01); *H01J 49/40* (2013.01); *H01J 49/427* (2013.01)

(58) Field of Classification Search
CPC .. H01J 49/14; H01J 49/24; H01J 49/40; H01J 49/427
USPC ................................ 250/281, 282, 283, 290
See application file for complete search history.

(56) References Cited

U.S. PATENT DOCUMENTS

2018/0328886 A1* 11/2018 Yasuno ................ G01N 27/622
2018/0340910 A1* 11/2018 Betz ..................... G01N 27/622

* cited by examiner

*Primary Examiner* — Nicole M Ippolito
(74) *Attorney, Agent, or Firm* — Liang IP, PLLC (57) ABSTRACT

Ion mobility spectrometry (IMS) systems, devices, and associated methods of operation are disclosed herein. In one embodiment, an IMS system includes an ionization region configured to receive and ionize a sample into ionized molecules and a detector configured to detect ionized molecules. The IMS system also includes a drift region in between and directly coupled to both the ionization region and the detector. The drift tube includes a first ion gate proximate the ionization region and a second ion gate proximate the detector. The first and second ion gates are configured to alternately introduce a batch of ionized molecules toward the detector while the other is maintained open, thereby allowing accurate measurement of a drift time of the ionized molecules corresponding to a drift length that is a distance between the first and second ion gates.

19 Claims, 6 Drawing Sheets

HIGH ACCURACY ION MOBILITY SPECTROMETRY

CROSS-REFERENCE TO RELATED APPLICATION(S)

This application claims priority to U.S. Provisional Application No. 62/518,098, filed on Jun. 12, 2017, the disclosure of which is incorporated herein by reference in its entirety.

STATEMENT REGARDING FEDERALLY SPONSORED RESEARCH

This invention was made with government support under grant no. W911NF-12-1-0575 awarded by the United States Army Research Laboratory through the Army Research Office. The government has certain rights in the invention.

BACKGROUND

Ion Mobility Spectrometry (IMS) is an analytical technique that has been used for military or security purposes, such as for detecting drugs and explosives. IMS is based on separation and identification of ionized molecules according to ion mobility of the ionized molecules under an applied electrical field. In a simplest form, IMS measures how long ions of a sample traverse a given length in a drift tube driven by the applied electric field. During operation, in specified intervals, a batch of the ions are introduced into the drift tube. The applied electric field then drives the ions through the drift tube during which the ions separate based on corresponding ion mobility values. The separated ions then arrive at a detector (e.g., a Faraday plate or mass spectrometer) to be recorded as a profile in order from the fastest to the slowest ions. The recorded profile, or a mobility spectrum, can represent a characteristic signal for a chemical composition in the sample. As such, the chemical composition in the sample can be identified.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

IMS techniques are based on separating and identifying gas phase ions according to corresponding size-to-charge ratios (Q/z). The size of an ion is related to its mobility (K) according to the Mason-Schamp equation, as follows:

$$K = \frac{3}{16}\sqrt{\frac{2\pi}{\mu k T}}\frac{Q}{n\sigma} \quad \text{(Equation 1)}$$

where K is the mobility of the ion, Q is the charge of the ion, n is the number density of a neutral drift gas, $\mu$ is the reduced mass of the ion and the neutral drift gas, k is the Boltzmann constant, T is the effective temperature of the drift gas, and $\sigma$ is the collision cross section of the ion-neutral interaction. IMS can be used to identify a target compound based on reduced mobility ($K_0$) values, as follows:

$$K_o = \frac{L^2}{Vt_d}\frac{P}{760}\frac{273.15}{T} \quad \text{(Equation 2)}$$

where L is the length of the drift length, V is the voltage (V) applied across L, $t_d$ is the drift time of the ion, T is the temperature (K) of the drift gas, and P is the pressure (Torr) of the drift gas.

To detect a target compound, field-deployed systems calculate the $K_0$ value of the unknown ion based on Equation 2. If the $K_0$ value appears within a predetermined detection window, set at the factory, an alarm for the corresponding target compound is sounded. Variations in instrument design, temperature, and pressure can cause variations in the calculation of the $K_0$ values determined by Equation 2. The $K_0$ values of the chemical standards used for factory calibration are an average of mobility values from a variety of ion mobility spectrometers under a variety of conditions. This necessitates the use of wide detection windows to avoid false negative responses. However, as a result of increasing the detection window width to ensure a true positive response, risks of false positive alarms can be increased. Any interferent with a similar $K_0$ value as the target compound of interest may appear within the detection window and signal an alarm. Likewise, instruments cannot arbitrarily reduce widths of detection windows to eliminate false positive alarms. This is because a true spectral peak may be excluded from a narrower window.

To the knowledge of the inventors, there is currently no method to calibrate an IMS instrument in the field, and factory calibration is the only calibration of the mobility scale for the duration of the detector life span. The most common instrument calibration method recommended by researchers has been to use a reference standard to calculate an instrument factor (Ci) for each instrument, as follows:

$$C_i = K_0 t_d = \frac{L^2}{V_i}\left(\frac{273.15}{T_i}\right)\left(\frac{P_i}{760}\right) \quad \text{(Equation 3)}$$

The $C_i$ value can be calculated using any ion. Therefore, a reference standard with a known $K_0$ value would serve to predict the $K_0$ value of a target compound as follows:

$$\frac{(K_{0\,std})\,t_{d\,std}}{t_{d\,coi}} = \frac{C_i}{t_{d\,coi}} = K_{0\,coi} \quad \text{(Equation 4)}$$

where $K_{0\,std}$ is the known $K_0$ value of a standard, $t_{d\,std}$ is the measured drift time of the standard, and $t_{d\,coi}$ is the drift time of the unidentified compound of interest. However, Equation 4 is only as accurate as the value of $K_{0\,std}$ used within the equation, and the inaccuracy of $K_{0\,std}$ is carried through to the calculation of $K_{0\,coi}$. As such, accuracy of standard $K_0$ values used to predict the $K_0$ values of the target compound is a contributor to the width of the detection window.

The $K_0$ values of various compounds of interest may be found in the literature, but accurate values may be absent. For example, both the reported accuracy and precision of $K_0$ values may be scarce. There is also a lack of precision in the individual variables. This produces a wide range of reported values for compounds analyzed under similar conditions. This uncertainty in $K_0$ values for IMS may lead to an average estimated accuracy of approximately ±0.02 cm² V⁻¹ s⁻¹, or ±2%, in the $K_0$ value of field IMS-based instruments.

Several embodiments of the disclosed technology provide an IMS instrument and associated methods of operations that can reduce errors of IMS measurements by implementing a drift tube with two ion gates spaced apart from each other in the drift tube. In certain embodiments, during a first stage of operation, a first ion gate proximate to an ionization region can be pulsed open for a period (e.g., every 200 μs) to introduce a batch of ionized molecules of a sample into the drift tube. An applied electric field in the drift tube can then separate and drive the ionized molecules toward the second ion gate proximate to a detector. During this stage, the second ion gate is maintained open to allow the separated ionized molecules to be detected by the detector (e.g., a Faraday plate or a mass spectrometer) proximate the second ion gate to generate a first profile of drift time measurements.

Once sufficient data of the first profile of drift time measurements is collected from the detector, the IMS system can initialize a second stage of operation in which the first ion gate is maintained open while the second ion gate is pulsed open for a period (e.g., every 200 μs). As such, the ionization region is effectively extended until the position of the second ion gate and the drift region is effectively shortened from the position of the second ion gate to the detector. Pulsing the second ion gate can introduce batches of the ionized molecules toward the detector under the applied electric field. The detector can then detect the introduced ionized molecules to generate a second profile of additional drift time measurements. The second profile of additional drift time measurements can then be subtracted from the first profile of drift time measurements to generate highly accurate drift time measurements corresponding to an accurately measured drift length that is the distance between the first and second ion gates.

Without being bound by theory, it is believed that an accurate correspondence between drift time measurements and a drift length can yield highly accurate ion mobility measurements (e.g., with errors less than about 0.5%). In certain IMS systems, a length between (i) an ion gate at one end of a drift tube and configured to introduce batches of ionized molecules into the drift tube and (ii) a detector such as a Faraday plate at another end of the drift tube is used as a drift length for drift time measurements. However, the inventors have recognized that such an assumption may not be valid at least because process conditions proximate to the detector may not be the same as those in the drift tube. For example, an IMS system may include a time of flight mass spectrometer (TOFMS) that uses a vacuum during measurements. The vacuum may cause the ionized molecules to drift differently proximate to the TOFMS than in the drift tube. As such, it is difficult to accurately measure the length of the ion path inside the TOFMS and the measured drift time may be skewed due to such differences in process conditions. Thus, by controlling the first and second ion gates as described above, an accurate correspondence of drift length and drift time can be obtained to yield highly accurate ion mobility measurements. In doing so, it was found during experiments that the error in the measurement of drift time was reduced from about ±2% to about ±0.2%.

DETAILED DESCRIPTION

Various embodiments of high accuracy ion mobility spectrometry systems, devices, and associated methods of operation are described below. In the following description, specific details of components and operations are included to provide a thorough understanding of certain embodiments of the disclosed technology. A person skilled in the relevant art will also understand that the technology may have additional embodiments, and that the technology may be practiced without several of the details of the embodiments described below with reference to FIGS. 1A-4.

As used herein, the term "ion mobility spectrometry" generally refer to an analytical technique for separating and identifying ionized molecules based on ion mobility in a drift medium. Example IMS systems are described below with particular operating parameters for illustration purposes only. Other embodiments of IMS systems in accordance with the present technology may also operate at low pressures (e.g., from about 1 mbar to about 20 mbar), at high pressure (e.g., 1013 mbar), at low temperatures (e.g., room temperature), at high temperatures (e.g., about 100° C. to about 200° C.), with different types of drift media (e.g. liquids, supercritical gases, and gases) with different compositions of drift medium (e.g., compressed air, helium, nitrogen, argon, carbon dioxide, etc.), with different drift tube designs, and/or at other suitable conditions.

Inaccurate and/or imprecise IMS reference measurements can lead IMS instruments to use wide detection windows to avoid excluding a peak of interest and to ensure low false negative response rates. However, as a result of increasing the detection window width to ensure a true positive response, false positive alarms can be increased. Any interferent with a similar drift time as the target compound of interest may appear within the detection window and signal an alarm. Likewise, instruments cannot arbitrarily reduce widths of detection windows to eliminate false positive alarms. This is because a true spectral peak may be excluded from a narrower window.

Several embodiments of the disclosed technology provide an IMS instrument and associated methods of operations that can reduce errors of IMS measurements by implementing a drift tube with two ion gates spaced apart from each other in the drift tube. In certain embodiments, during a first stage of operation, a first ion gate proximate to an ionization region can be pulsed open for a period (e.g., every 200 μs) to introduce a batch of ionized molecules of a sample into the drift tube. An applied electric field in the drift tube can then separate and drive the ionized molecules toward the second ion gate proximate to a detector. During this stage, the second ion gate is maintained open to allow the separated ionized molecules to be detected by the detector (e.g., a Faraday plate or a mass spectrometer) proximate the second ion gate to generate a first profile of drift time measurements.

Once sufficient data of the first profile of drift time measurements is collected from the detector, the IMS system can initialize a second stage of operation in which the first ion gate is maintained open while the second ion gate is pulsed open for a period (e.g., every 200 μs). As such, the ionization region is effectively extended until the position of the second ion gate and the drift region is effectively shortened from the position of the second ion gate to the detector. Pulsing the second ion gate can introduce batches of the ionized molecules toward the detector under the applied electric field. The detector can then detect the introduced ionized molecules to generate a second profile of additional drift time measurements. The second profile of additional drift time measurements can then be subtracted from the first profile drift time measurements to generate highly accurate drift time measurements corresponding to a drift length that is the distance between the first and second ion gates.

Without being bound by theory, it is believed that an accurate correspondence between drift time measurements and a drift length can yield highly accurate ion mobility measurements (e.g., with errors less than about 0.5%). In certain IMS systems, a length between (i) an ion gate at one end of a drift tube and configured to introduce batches of ionized molecules into the drift tube and (ii) a detector such as a Faraday plate at another end of the drift tube is used as a drift length for drift time measurements. However, the inventors have recognized that such an assumption may not be valid at least because process conditions proximate to the detector may not be the same as those in the drift tube. For example, an IMS system may include a time of flight mass spectrometer (TOFMS) that uses a vacuum during measurements. The vacuum may cause the ionized molecules to drift differently proximate to the TOFMS than in the drift tube. As such, it is difficult to accurately measure the length of the ion path inside the TOFMS and the measured drift time may be skewed due to such differences in process conditions. Thus, by controlling the first and second ion gates as described above, an accurate correspondence of drift length and drift time can be obtained to yield highly accurate ion mobility measurements, as described in more detail below with reference to FIGS. 1A-4.

Figure 1A:
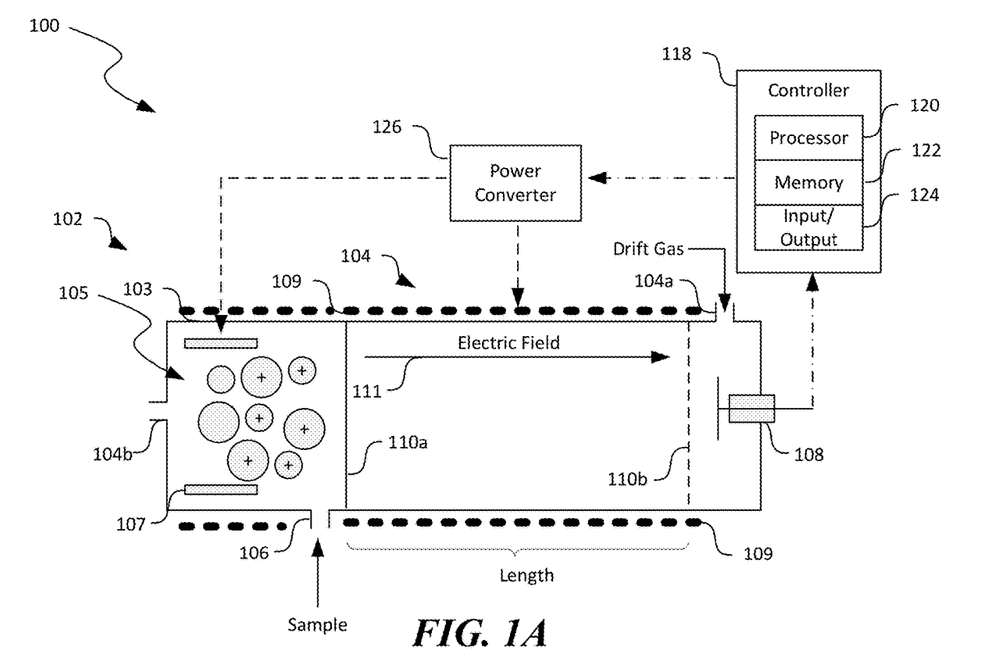
FIGS. 1A-1E are schematic diagrams of an IMS system configured for high accuracy ion mobility spectrometry in accordance with embodiments of the present technology.

FIGS. 1A-1E are schematic diagrams of an IMS system 100 configured for high accuracy ion mobility spectrometry in accordance with embodiments of the present technology. As shown in FIG. 1A, the IMS system 100 can include a drift tube 102 having an ionization region 103 and a drift region 104, a detector 108, a controller 118, and a power converter 126 operatively coupled to one another. Even though only the foregoing components are shown in FIG. 1A, in other embodiments, the IMS system 100 can also include pressure controllers, temperature controllers, and/or other suitable components.

The power converter 126 can be configured to supply a voltage and/or current to the drift tube 102 and ionization source 107 (shown schematically as a pair of charging plates) to induce ionization in the ionization region 103 as well as establishing an electric field 111 in the drift tube 102. The power converter 126 can individually include a buck, a boost, an inverting, a flywheel, and/or other suitable types of voltage and/or current power converter. The ionization source 107 can include a radioactive Ni-63, a corona needle, or other suitable ionization components. In the illustrated embodiment, the power converter 126 is shown as supplying power to both the ionization region 103 and the drift region 104. In other embodiments, the IMS system 100 can also include additional power converters (not shown) in addition to the power converter 126 to, for instance, provide an electrical bias to the ionization source 107.

The ionization region 103 can include a reaction zone 105 having a sample inlet 106. In operation, a sample (with or without a carrier gas) may be injected into the reaction zone 105 via the sample inlet 106. The injected sample can then be at least partially ionized in the reaction zone 105 before flowing toward the drift region 104. In the illustrated embodiment, the ionization region 103 is directly coupled to the drift region 104 to form a unitary body drift tube 102. In other embodiments, the ionization region 103 may be coupled to the drift region 104 via pipes, tubes, and/or other suitable conduits. Though the ionized molecules are shown as positive ions in FIG. 1A for illustration purposes, in other embodiments, the ionized molecules can also be negative ions depending on a suitable application.

The drift tube 102 can include a drift medium inlet 104a, a drift medium outlet 104b, and an electric field generator 109 electrically coupled to the power converter 126. In operation, the power converter 126 applies a voltage and/or current bias to the electric field generator 109 having, for instance, multiple electrode rings spaced apart from one another, which in turn generates an electric field 111 in the drift tube 102. In one embodiment, the electric field 111 can be generally uniform in the drift tube 102. In other embodiments, the electric field 111 may have other suitable distribution profiles between the ionization region 103 and the drift region 104. Even though the electric field generator 109 is shown in FIG. 1 as two parallel series of electrodes spaced apart from the drift medium inlet and outlet 104a and 104b, in other embodiments, the electric field generator 109 may include two plates, a radio frequency generators, and/or other suitable components capable of generating an electric field in the drift tube 102.

As shown in FIG. 1A, the drift tube 102 can include a first ion gate 110a proximate the ionization region 103 and a second ion gate 110b proximate the detector 108. The first and second ion gates 110a and 110b are collectively referred to as ion gates 110 herein. The ion gates 110 can be individually configured to stop or allow ionized molecules from passing through the ion gates 110 based on an applied control signal from, for instance, the controller 118. In the FIGS. 1A-1E, the ion gates 110 are shown as a solid line when closed and a dashed line when open. The ion gates 110 can be a Bradbury-Nielson (BN), Tyndall-Powell (TP), or other suitable types of design. As described in more detail below, the controller 118 can be configured to apply a control signal to the ion gates 110 for highly accurate ion mobility measurements.

In certain embodiments, the detector 108 can include a Faraday plate. In other embodiments, the detector 108 can include a mass spectrometer and/or other suitable components for detecting/identifying ions flowing through the drift region 104. In one embodiment, ions are recorded at the detector 108 from the fastest to the slowest to generate a response signal (e.g., a current versus time signal) characteristic for a chemical composition of the measured sample. In other embodiments, ions may be recorded and/or detected via other suitable techniques.

The controller 118 can include a processor 120 coupled to a memory 122 and an input/output component 124. The processor 120 can include a microprocessor, a field-programmable gate array, and/or other suitable logic devices. The memory 122 can include non-transitory volatile and/or nonvolatile media (e.g., ROM; RAM, magnetic disk storage media; optical storage media; flash memory devices, and/or other suitable storage media) and/or other types of computer-readable storage media configured to store data received from, as well as instructions for, the processor 120 (e.g., instructions for performing the methods discussed below with reference to FIG. 4). The input/output component 124 can include a display, a touch screen, a keyboard, a mouse, and/or other suitable types of input/output devices configured to accept input from and provide output to an operator.

In certain embodiments, the controller 118 can include a personal computer operatively coupled to the other components of the IMS system 100 via a communication link (e.g., a USB link, an Ethernet link, a Bluetooth link, etc.) In other embodiments, the controller 118 can include a network server operatively coupled to the other components of the IMS system 100 via a network connection (e.g., an internet connection, an intranet connection, etc.) In further embodiments, the controller 118 can include a process logic controller, a distributed control system, and/or other suitable computing frameworks.

FIG. 1A illustrates a first operating stage of the IMS system 100 in which the first ion gate 110*a* is pulsed while the second ion gate 110*b* is open. For example, as shown in FIG. 1A, the sample can be introduced to the ionization region 103. The power converter 126 can apply a voltage to the ionization source 107 to generate the ionized molecules in the ionization region 103 (shown as positive ions). At a first time point, the controller 118 can provide a control signal to the first ion gate 110*a* to cause the first ion gate 110*a* be closed. As such, no ionized molecules are introduced into the drift region 104.

Figure 1B:
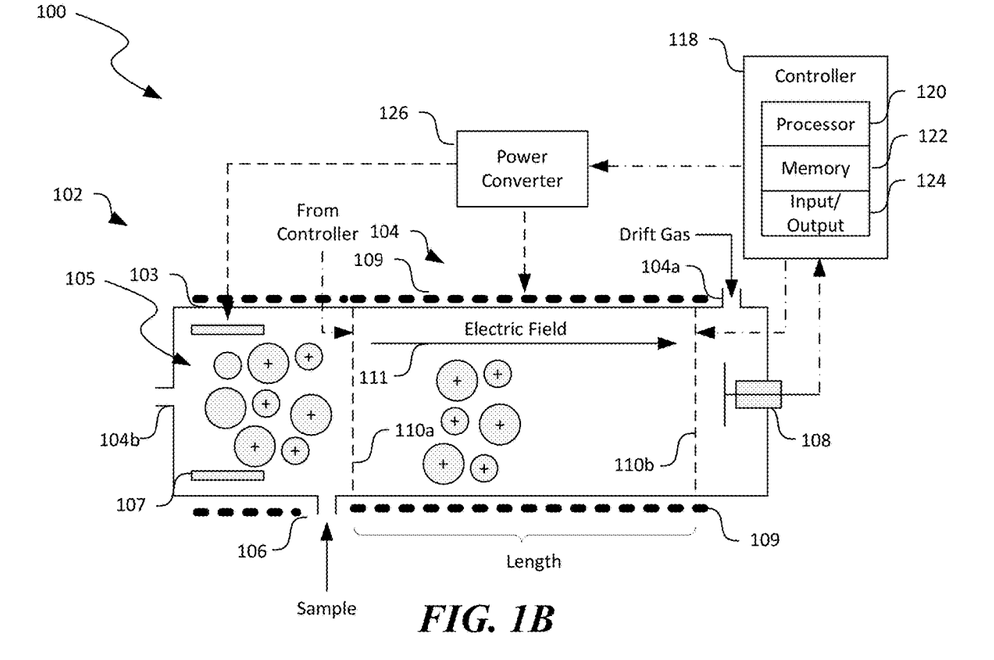

As shown in FIG. 1B, at a second time point, the controller 118 can provide another control signal to the first ion gate 110*a* to cause the first ion gate 110*a* to be open for a period of time (e.g., 200 μs). Opening of the first ion gate 110*a* can thus introduce a batch of ionized molecules into the drift region 104. The power converter 126 can apply a voltage to the electric field generator 109 to apply an electric field 111 to the ionized molecules in the drift region 104. The applied electric field 111 can then drive the ionized molecules toward the second ion gate 110*b* through a counter-flowing drift gas while the ionized molecules are separated according to corresponding ion mobility in the electric field 111.

Figure 1C:
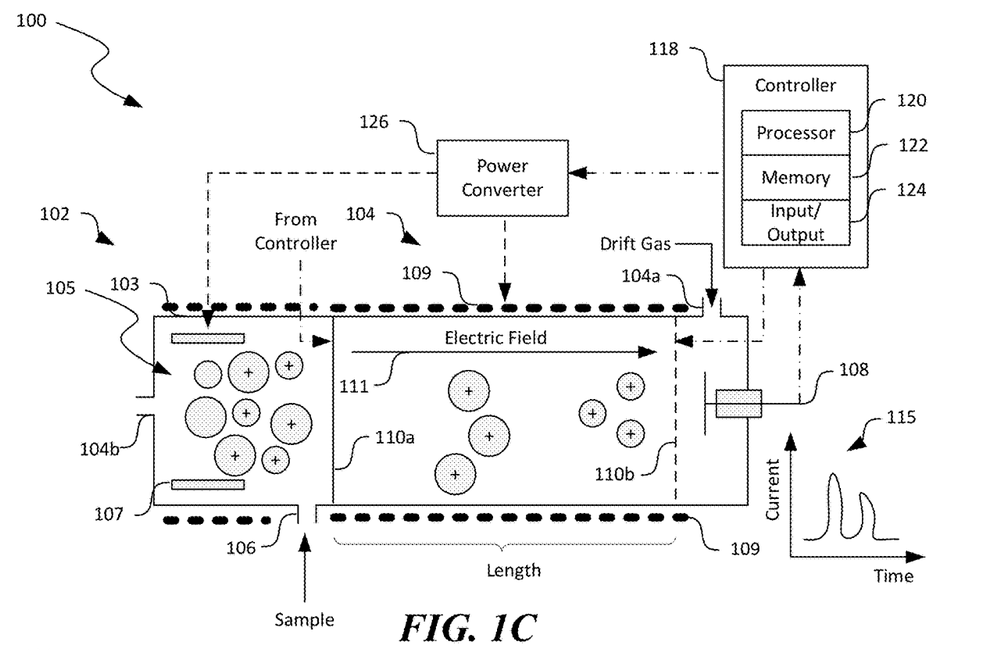

The separated ionized molecules can then travel through the second ion gate 110*b* and reach the detector 108 to be recorded by the controller 118 to generate a drift time as a number of charges/current versus time plot 115, as shown in FIG. 1C. The controller 118 can then repeat the pulsing of the first ion gate 110*a* and recording the drift time until sufficient data of the drift time of the sample is obtained.

Figure 1D:
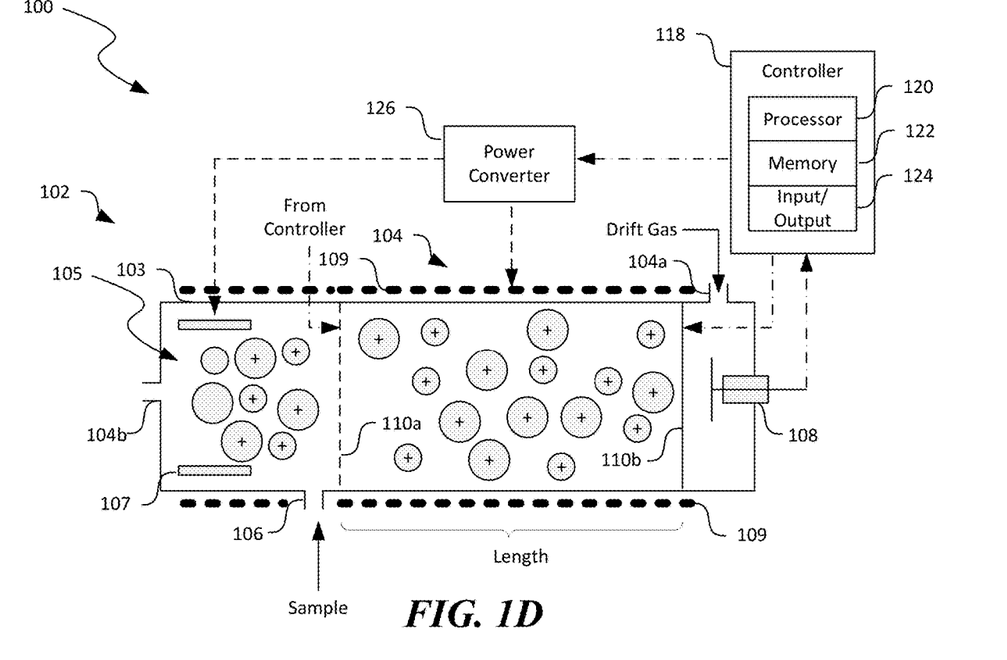
Figure 1E:
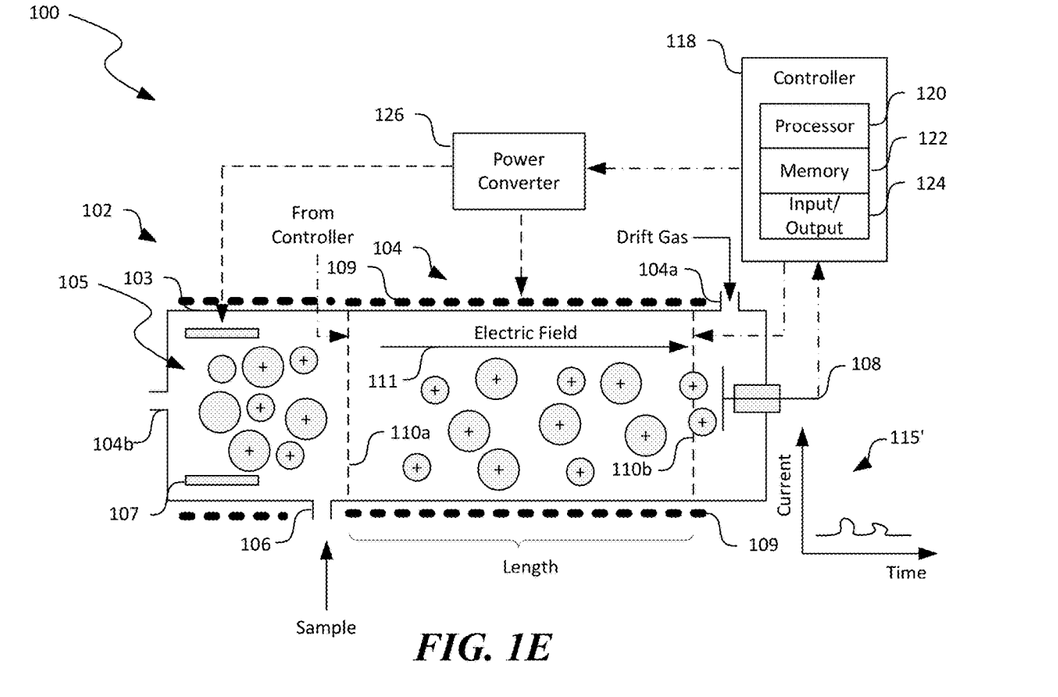

The controller 118 can then proceed to another stage of the operation for enhancing accuracy of the obtained drift time. As shown in FIG. 1D, the controller 118 can provide additional control signals to the first and second ion gates 110*a* and 110*b* to cause the first ion gate 110*a* to be open while the second ion gate 110*b* is pulsed. Thus, at a first time point, the drift region 104 can be filled with ionized molecules from the ionization region 103 while the first ion gate 110*a* is open and the second ion gate 110*b* is closed. As shown in FIG. 1E, at a second time point, the second ion gate 110*b* can be opened for a period of time (e.g., 200 μs) while the power converter 126 applies a voltage to the electric filed generator 109 to generate the electric field 111 in the drift region 104. As such, a batch of the ionized molecules can be introduced through the second ion gate 110*b* toward the detector 108 to be recorded as additional drift time 115'. The controller 118 can then repeat pulsing the second ion gate 110*b* while the first ion gate 110*a* is open to collect sufficient data.

In accordance with several embodiments of the disclosed technology, the additional drift time 115' can then be subtracted, for instance, by the controller 118, from the original drift time 115 to derive an accurate drift time for the ionized molecules for traveling a length that equals to a distance between the first and second ion gates 110*a* and 110*b*. The inventors have recognized that in certain IMS systems, a length between the first ion gate 110*a* and the detector 108 may not represent an accurate drift length for the ionized molecules because process conditions proximate to the detector 108 may not be the same as those in the drift region 104. For example, a vacuum may be used proximate to the detector 108 for collecting data of the drift time. As such, such measured drift time may be skewed due to such differences in process conditions. In contrast, process conditions between the first and second ion gates 110*a* and 110*b* can be controlled or maintained as generally homogeneous. As such, by subtracting the additional drift time 115' from the original drift time 115, the controller 118 can derive an accurate drift time directly corresponding to a drift length of the distance between the first and second ion gates 110*a* and 110*b*. Thus, a precise drift length and drift time correspondence can be obtained to yield highly accurate ion mobility measurements.

Certain experiments utilizing an implementation of the IMS system described above were conducted to generate comparison ion mobility measurements. As described in more detail below, the experiments showed that an approximately ten fold improvement in measurement error was obtained.

Figure 2:
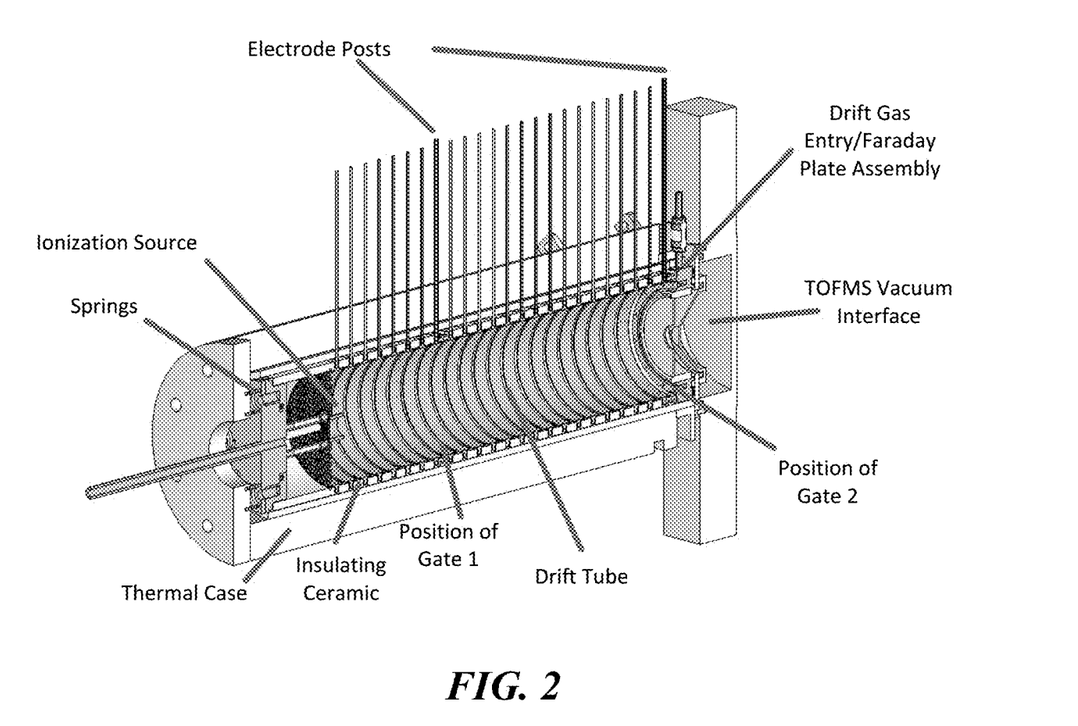
FIG. 2 is an isometric cut-away diagram illustrating an example IMS system configured for high accuracy ion mobility spectrometry in accordance with embodiments of the present technology.

FIG. 2 is an isometric cut-away diagram illustrating an example IMS system configured for high accuracy ion mobility spectrometry in accordance with embodiments of the present technology in accordance with embodiments of the present technology. As shown in FIG. 2, the IMS system includes a drift tube having two Bradbury-Nielson (BN) ion gates (shown as Gate 1 and Gate 2) used to initiate the drift time measurements. The two BN ion gates were used to designate the length of the drift tube as the distance between these two BN ion gates. The drift time of the ion therefore directly correlated to this length by measuring the drift time of the ion from each BN ion gate and taking the difference between these two drift time measurements. This produced the time the ion took to travel between each BN ion gate.

Each BN ion gate includes a single ceramic insulator ring cut in half radially, and ground into the outer face of each half ring was a 1.27 mm wide channel. One side of the channel was also ground down to have an o.d. of 66.18 mm. The smaller outside diameter faces of the two BN ion gate halves were then cemented together with an array of parallel 0.003" o.d. Alloy 46 wires (California Fine Wire Company, Grover Beach, Calif.), spaced 0.005" apart, between them. Alternating wires were electrically connected to create two interleaved sets of parallel and electrically isolated wires.

The last electrode before the time of flight mass spectrometer (TOFMS) vacuum interface served to introduce the neutral counter current flow of drift gas and also contained a Faraday plate for optional standalone analysis without the TOFMS as the detector. The drift gas was introduced using a showerhead design. The drift gas showerhead/Faraday plate assembly, shown in FIG. 2, was placed behind the second ion gate and just before the pressure interface of the TOFMS. The drift gas showerhead/Faraday plate assembly included a central annular Faraday plate cemented within a piece of insulating alumina tubing using Resbond 920 fast curing ceramic adhesive from Cotronics (Brooklyn, N.Y.), and the alumina tubing was likewise cemented within the outer drift gas entry showerhead.

On top of the showerhead were seated three different leads: the first being a metal to ceramic brazed isolator on the left from Solid Sealing Technology, Inc (Watervliet, New York). This isolator was hollow and served to allow for the attachment of a drift gas line using ⅛" Swagelok fittings while keeping the line electrically isolated from the voltage applied to the showerhead. The next two leads were on the right and were in line with one another along the axis of the drift tube. The lead in front was a BNC cable attached to a 1 kV feedthrough also from Solid Sealing Technology, Inc. The other end of the feedthrough was spot welded to the backside of the Faraday plate to complete the circuit for standalone Faraday plate analyses. The last lead behind the BNC cable lead was the threaded rod screwed into the showerhead to supply voltage to the showerhead from the resistor chain along the length of the drift tube. The overall outside diameter of the showerhead was the same as the ceramic insulator rings, and its front face was machined to create a 0.5 mm cavity when placed against the second ion gate, identical to cavities formed by the machined metal drift rings and the ceramic insulator rings.

To pressure seal each of the joints between the electrode and insulator rings, the two sections of the drift tube with continuous inner diameters (the drift region and reaction region, excluding the BN ion gates) were mounted separately onto an adjustable mandrel that was then tightly clamped down onto the mounted stack. The mandrel served to keep all drift rings in place during construction and ensure that the electrode rings were concentric and parallel to maintain a homogenous electric field. Resbond 920 fast curing ceramic adhesive was injected into the 0.5 mm cavities created by machined ridges in the metal drift rings. After allowing to air dry for twenty-four hours, each region was taken off the mandrel and heat cured in an oven at 150° C. for an additional twenty-four hours. A light layer of Duprot 801 ceramic potting material, also from Cotronics, was then applied to the cured cement to help strengthen the joints. Similarly, the layer of Durapot 801 was allowed to air dry and was then heat cured. After heat curing the Durapot 801, a layer of Celvaseal liquid vacuum leak sealant form Myers Vacuum (Kittanning, Pa.) was brushed onto the joints and allowed to air dry for two weeks.

After drying, each part was again placed in the oven to melt away excess Celvaseal and cure what had permeated into the micropores of the ceramic. The parts were then cleaned of excess Celvaseal using dichloromethane and cotton tipped applicators. This left a layer of Celvaseal cured within the micropores of the drift tube joints. A second layer of Durapot 801 was then applied to the dried layer of Celvaseal to encase the vacuum seal layer. Special care was taken to ensure that the second layer of Durapot 801 did not extend past the outside diameter of the ceramic insulator rings. Parts that were unable to be mounted on the mandrel (the BN ion gates, showerhead, first electrode, and ionization source interface) were lined up within the rest of the assembly on the bench top and a 36" bar clamp was used to fasten the stack to the bench top. This ensured a tight mating of all faces and prevented the rings from separating while injecting the ceramic cement into the remaining joints. The same sealing procedure was then repeated for the remaining joints.

Figure 3A:
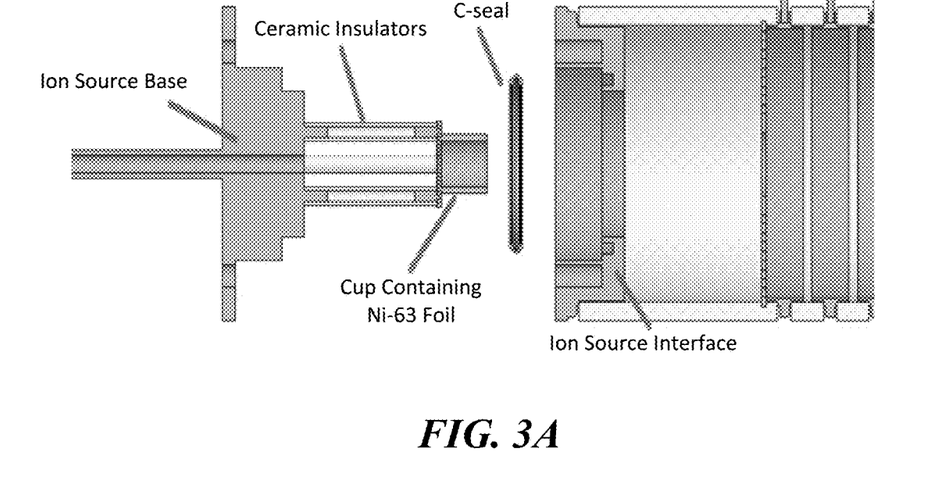
FIGS. 3A and 3B are cross-sectional diagrams of a portion of the example IMS system in FIG. 2 before and after assembly.
Figure 3B:
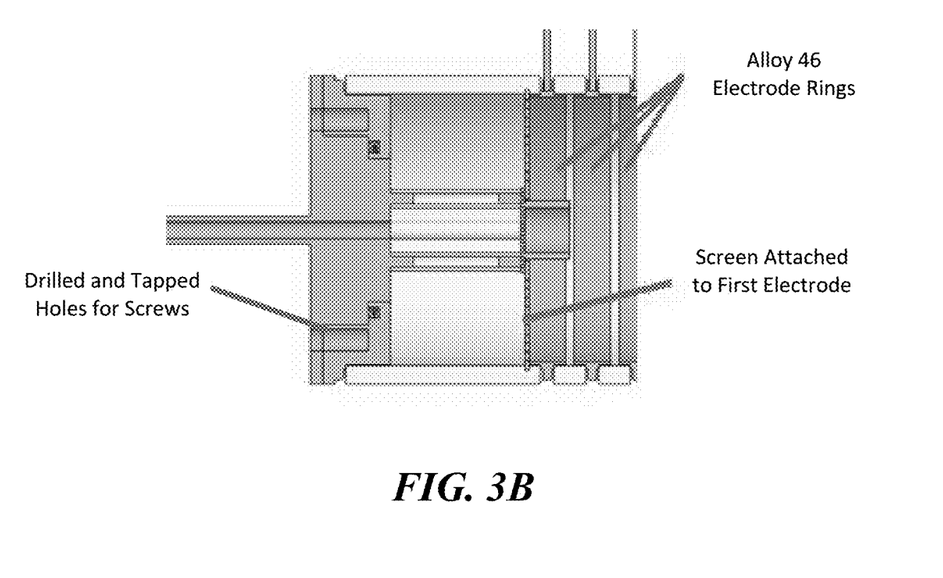

As shown in FIGS. 3A and 3B, the front end of the drift tube was sealed by a 39.7 mm o.d. by 34.5 mm i.d. c-Seal. The c-Seal was compressed by screwing down the ion source front plate using eight socket cap screws. Four springs from McMaster-Carr, each with a force of 19 lbs/ft, were mounted equidistantly around four of the screws on the ion source front plate and compressed between the ion source front plate and the front plate of the thermal case holding the IMS instrument assembly. These springs pushed the IMS instrument up against the front of the TOFMS and compressed a 2.25" i.d. x-profile double sealing o-ring that was placed around a seating ridge on the back of the drift gas showerhead. This double sealing o-ring created a pressure seal between the back of the showerhead and the front of the TOFMS vacuum interface. The IMS instrument is housed within an insulating ceramic tube, which was in turn housed within an aluminum thermal case. The thermal case was attached to the TOFMS vacuum interface using screws and thumb nuts.

Compressed air was introduced as the drift gas at a rate of 1.00±0.01 L/min using an 1179 A digital mass flow controller, and a 640 A pressure controller established non-ambient pressures. The mass flow and pressure controllers were powered and set by a 247D four-channel power supply and display. The gas outlet of the IMS instrument was connected to a DS 42 dual stage rotary vane vacuum pump from Ideal Vacuum Products (Albuquerque, N. Mex.). To obtain sub-ambient pressures, the vacuum pump was turned on and an orifice within the pressure controller restricted the flow of gas evacuating from the drift tube to establish the pressure set on the 247D power supply and read out. The vacuum pump was disconnected from the gas outlet when conducting ambient pressure studies.

Volatile headspace vapor samples were introduced into the instrument by placing 0.5 μL of the sample in a ⅛" Swagelok cap and attaching the cap to the bottom of an 8" length of stainless steel tubing. The sample tee was connected via Swagelok fittings to a compressed air gas tank on one side and to a 250 μm i.d. by 360 μm o.d. fused silica capillary from Polymicro Technologies (Lisle, Ill.) via Valco fittings on the other. The capillary was inserted through the hollow electrode post, which also served as a temperature probe port during experiment set up, in front of the first BN ion gate and terminated in the reaction region in the center of the drift tube diameter. The capillary was held in place in the hollow electrode by a Valco fitting adapted for electrical continuity. The orthogonal flow of gas carried the headspace vapors rising from the sample tee through the silica capillary and into the reaction region of the accurate IMS instrument. A 15 kV ceramic isolator from Solid Sealing Technology, Inc served to electrically isolate the drift tube from the sample tee.

Without being bound by theory, it is believed that the degree of error in calculating $K_0$ values with an IMS instrument is dependent upon the measured accuracies of the components within the IMS system as they relate to the five variables of Equation (2) above: length (L, cm), voltage (V, V), drift time (td, ms), temperature (T, K), and pressure (P, Torr).

The length of the drift tube was defined as the distance from the first BN ion gate wires to the second BN ion gate wires. The length between BN ion gates wires was calculated by taking the sum of three length measurements at room temperature. Half of each gate and the length of the drift tube between both BN gates. Length was measured by a pair of 12 inch calipers from Mitutoyo (Aurora, Ill.) with an error of ±0.0015 in (±0.0381 mm). All length measurements were corrected for thermal expansion.

Voltage was supplied to the drift tube by an LS020 reversible 20 kV power converter from Exelis (West Springfield, Mass.). The electric field (E) within the IMS instrument was set up to be homogenous and adjustable from the first electrode to the inlet of the TOFMS, with the electric field terminating at the same potential as the inlet of the TOFMS. A series of 20 MΩ resistors (Caddock Electronics Inc., Riverside, Calif., ±1%) were attached between electrode rings via pin connectors from Positronic Industries Inc. (Springfield, Mo.). A 5 MΩ variable resistor (Newark, Chicago, Ill.) was attached as a potentiometer across the showerhead (SH) after the second BN ion gate, and a second series of 5 MΩ variable resistors leading to ground were attached to the end of the resistor chain to establish the electric field. The electric field was set to the desired value by adjusting the voltage applied to the first ring and the total resistance of the chain after the potentiometer. 10 MΩ resistors (±1%) from Caddock were also used across the first BN ion gate and leading up to the second BN ion gate reference instead of 20 MΩ resistors.

The voltage across the drift space was measured using an 8846 A digital multimeter (DMM) from Fluke (Everett, Wash.). The DMM had an accuracy of ±0.0024% of the measurement plus 0.0005% of the DMM range used. The DMM was coupled with a 10 GΩ high precision HVP-250 voltage divider from Computer Power Supplies (Tigard, Oreg.) with an accuracy of ±0.05% over the full measurement. The divider had a ratio of 10,000:1 (measured directly to $1.003 \times 10^{-4} \pm 5 \times 10^{-7}$) and required the DMM to be used in high input impedance mode when measuring voltage due to the resulting input voltage being less than 1 V.

The power converter had such a low output current that it required the use of higher resistors in the electric field. However, because the 10 GΩ voltage divider had a comparably high resistance to that of the total resistor chain on the IMS instrument, it offered the current running through the resistor chain an alternate path to ground of near equivalent resistance and drew down the observed voltage measurement when the probe was applied. This necessitated a correction to the measurement obtained from the DMM to determine the "true" voltage at that point. The corrected voltage difference between the first and second BN ion gate reference voltages was used in reduced mobility calculations to correspond with the length measured between BN ion gate wires.

The drift time was measured using two methods for comparative purposes. The first method for measuring drift time used the TOFMS to record two separate drift times; the first drift time from the first BN ion gate and the second drift time measured from the second BN ion gate. The drift time between the two BN ion gates was determined by taking the difference between the two drift time measurements, and the time spent past the second BN ion gate and within the TOFMS was thereby eliminated. In this manner the drift time measurement between the two BN ion gates directly corresponded with the measured length between the two BN ion gates. The second method of drift time measurement was to use the first BN ion gate and the Faraday plate, with the second BN ion gate acting as an aperture grid.

The IMS instrument was heated by two 25.5 cm long heater cartridges from Heatcon (Seattle, Wash.) inserted into the aluminum thermal case. The heater cartridges were controlled by a pair of CN7823 DIN temperature controllers from Omega (Norwalk, Conn.). The temperature controllers measured the temperature of the thermal case using a pair of RTD-850 resistive temperature devices embedded in the thermal case. The temperature controllers had an output accuracy of ±0.1° C. and the RTDs had a measurement accuracy of ±0.15° C. The thermal case was insulated by a custom-built insulation sleeve from LCS Isotherm (Frankfurt, Germany).

Preheating the drift gas above the desired temperature before it entered the showerhead reduced the temperature gradient within the drift tube. This compensated for the heat sink behind the IMS instrument created by the TOFMS. The drift gas was preheated using a heater built in house at WSU, consisting of an eight inch length of stainless steel tubing wrapped with three feet of 90 Ω/ft resistance wire, and covered in a protective outer sheath. A Variac supplied a constant voltage to the heater through an electrical plug connected to the resistance wire.

The temperature value of the drift gas used in reduced mobility calculations was measured by two T100-250 probes with an accuracy of ±0.01° C. coupled to an F 200 precision thermometer; both were from Isotech (Colchester, Vt.). Each probe was inserted into the drift space through the two hollow electrode posts in front of each BN ion gate, after removing the attached resistor pins and caps.

Ambient pressure (approximately 697 Torr for Pullman, Wash.) was measured by a 230-7420 mercury barometer from NovaLynx (Grass Valley, Calif.). The barometer had an accuracy of ±0.2 Torr after correcting for temperature and gravity at the measurement site. A 640 A pressure controller from MKS Instruments (Andover, Mass.) containing a capacitance manometer and with an accuracy of ±0.5% was also used for comparison to the reading. The counter current drift gas was maintained at 1.00±0.01 L/min with an 1179 A digital mass flow controller and 247D four channel power supply and display, also from MKS instruments.

The performance of the instrument and accuracy of each of the five variables in the reduced mobility Equation (2) was assessed, as described in turn below:

Length

The length from the first to the second BN ion gate wires at room temperature was measured to be 15.977±0.007 cm and was adjusted for thermal expansion as temperature was changed, with an error of ±0.04%.

Voltage

Due to the ratio of resistance values, the voltage measured on the first electrode did not require any correction apart from the divider ratio of the HV probe, which was also directly measured. When the voltage on the first electrode was measured and used to predict the resulting voltages at both BN ion gate references, the difference between the calculated "true" measurements was within 0.02% of the predicted difference. This supports the notion that the "true" voltages were valid and the voltage measurement was accurate.

Drift Time

Ion drift time was measured from both BN ion gate 1 and BN ion gate 2 and the time spent in the TOFMS was eliminated by taking the difference between the two measurements. In doing so, the length traveled by the ions was directly correlated to the drift time within that length.

Pressure

Ambient pressure measurements made with the barometer were corrected for temperature and gravitational force, resulting in a pressure that was 2.5 Torr less than the measured value. This correlates to an error of approximately ±0.03% for pressure measurements using the barometer.

Temperature

The largest source of error when using a TOFMS in tandem with an IMS instrument is the temperature gradient that forms as a result of the TOFMS acting as a heat sink behind the IMS instrument. When the drift gas preheater was used in conjunction with the thermal case's temperature controller, the temperature gradients within the drift region were reduced to less than 0.1° C. for all temperatures studied. The temperature used for reduced mobility calculations was then taken to be the average value between the two measurement points, with the error being half the gradient between measurement points. The highest gradient correlates to an error of ±0.04%.

During experiments, $K_0$ values were reported to at least ±0.2% or better. This is more than an order of magnitude improvement upon previously reported accuracies for measurements of $K_0$ values, as shown in the Table below:

| Variable (units) | Error | Source of Largest Error |
|---|---|---|
| L (cm) | $S_L = \frac{0.007 \text{ cm}}{16.252 \text{ cm}} = 4 \times 10^{-4}$ | Calipers |
| V (V) | $S_V = \frac{0.2 \text{ V}}{4533.1 \text{ V}} = 4 \times 10^{-5}$ | High Voltage Divider Probe and Digital Multimeter |
| $t_d$ (s) | $S_{t_d} = \frac{1 \times 10^{-9} \text{ s}}{1 \times 10^{-2} \text{ s}} = 1 \times 10^{-7}$ | tofMS clock rate |
| T (K) | $S_T = \frac{0.04 \text{ K}}{323.36 \text{ K}} = 1 \times 10^{-4}$ | Drift Gas Temperature Gradient |
| P (Torr) | $S_P = \frac{0.2 \text{ Torr}}{690 \text{ Torr}} = 3 \times 10^{-4}$ | Mercury Barometer |

Propagating the error associated with each variable in Table 1 produces an error of ±0.001 $cm^2V^{-1} s^{-1}$ for a $K_0$ value of 1 and ±0.002 $cm^2V^{-1} s^{-1}$ for a $K_0$ value of 2, amounting to an optimized error ±0.1% for $K_0$ value measurements.

Figure 4:
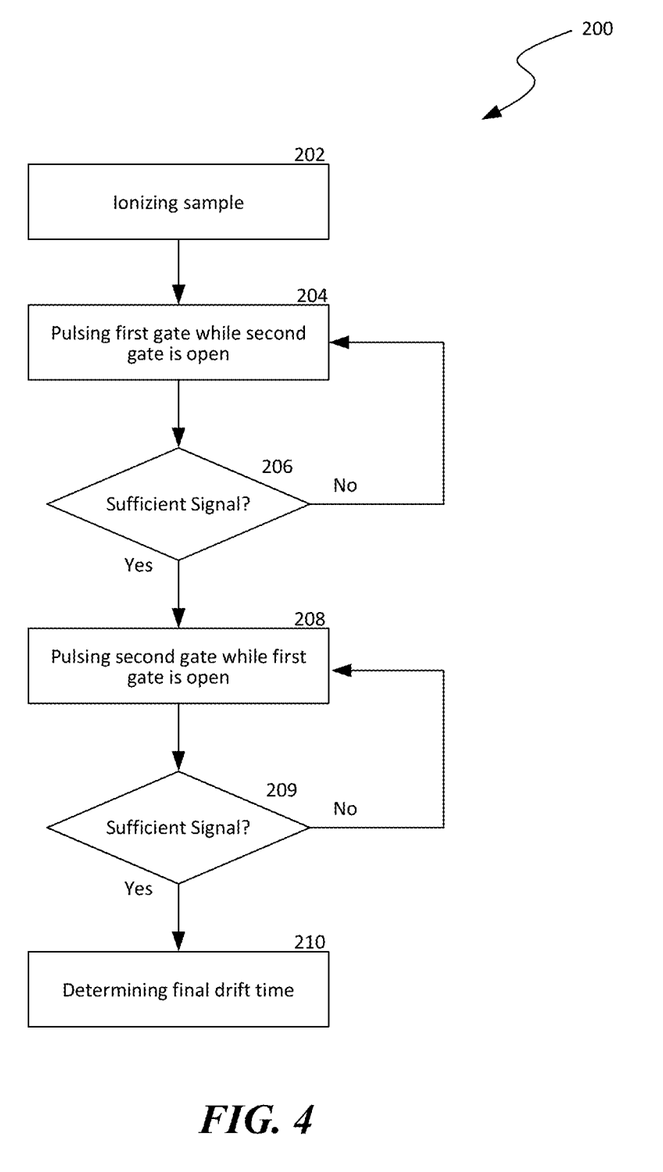
FIG. 4 is a flow chart illustrating a method of high accuracy ion mobility spectrometry in accordance with embodiments of the present technology.

FIG. 4 is a flow chart illustrating a method 200 of high accuracy ion mobility spectrometry in accordance with embodiments of the present technology. As shown in FIG. 4, the method 200 can include ionizing a sample in gas phase at stage 202. The method 200 can then include pulsing a first ion gate to introduce a batch of ionized molecules into a drift tube while a second ion gate proximate to a detector is open at stage 204. An electric field is applied in the drift tube to drive the ionized molecules toward the second ion gate and the detector. While moving toward the detector, the ionized molecules can separate according to corresponding $K_0$ values.

The method 200 can then include a decision stage 206 to determine whether sufficient drift time signal has been collected at the detector. In certain embodiments, the collected data is deemed sufficient when a preset number of data points are collected. In other embodiments, the collected data can be deemed sufficient based on other suitable criteria. In response to determining that the collected data is not sufficient, the method 200 reverts to pulsing the first ion gate at stage 204. Otherwise, the method 200 can include pulsing the second ion gate to introduce additional batches of ionized molecules from the drift tube toward the detector while the first ion gate is maintained open at stage 208. The method 200 can then include another decision stage 209 to determine whether sufficient drift time signal has been collected at the detector. In response to determining that the collected data is not sufficient, the method 200 reverts to pulsing the second ion gate at stage 208. Otherwise, the method 200 can proceed to determining a final drift time at stage 210. As such, additional data of the drift time past the second ion gate can be collected. The method 200 can then include determining a final drift time for a drift length between the first and second ion gates at stage 210. In one embodiment, the final drift time can be determined by subtracting the additional drift profile from the original drift profile. In other embodiments, the final drift time can be determined in other suitable manners based on the measured drift profiles.

From the foregoing, it will be appreciated that specific embodiments of the disclosure have been described herein for purposes of illustration, but that various modifications may be made without deviating from the disclosure. In addition, many of the elements of one embodiment may be combined with other embodiments in addition to or in lieu of the elements of the other embodiments. Accordingly, the technology is not limited except as by the appended claims.

We claim:

1. A method for performing ion mobility spectrometry in a drift tube having a first ion gate and a second ion gate along a drift direction of the drift tube, the method comprising:
   ionizing a sample into ionized molecules;
   opening a first ion gate for a period to introduce a batch of the ionized molecules into the drift region having an applied electric field, thereby moving the ionized molecules along the drift direction toward the second ion gate while the ionized molecules are separated according to corresponding ion mobility values;
   maintaining the second ion gate open to allow the ionized molecules to reach a detector proximate the second ion gate, the detector detects the ionized molecules and records a first drift time of the detected ionized molecules; and
   subsequently,
   maintaining the first ion gate open to allow the drift region being filled with additional ionized molecules;
   opening the second ion gate for another period to introduce another batch of the additional ionized molecules to the detector, thereby allowing the detector to detect another batch of ionized molecules and records a second drift time; and
   deriving a final drift time corresponding to a drift length between the first and second ion gates by subtracting the second drift time from the first drift times.

2. The method of claim 1 wherein the first and second ion gates individually include a Bradbury-Nielson or a Tyndall-Powell gate, and wherein maintaining and opening the first and second ion gates include providing a corresponding electrical control signal to the Bradbury-Nielson or a Tyndall-Powell gate.

3. The method of claim 1, further comprising:
   determining whether sufficient data of the first drift time is collected at the detector based on a preset number of data points; and
   in response to determining that sufficient data of the first drift time is not collected at the detector, repeating the opening of the first ion gate and maintaining the second ion gate open operations until sufficient data is collected.

4. The method of claim 1, further comprising:
   determining whether sufficient data of the first drift time is collected at the detector based on a preset number of data points; and
   in response to determining that sufficient data of the first drift time is collected at the detector, proceeding to maintaining the first ion gate open and opening the second ion gate for another period operations.

5. The method of claim 1 wherein opening the second ion gate for another period includes opening the second ion gate for another period to introduce another batch of the additional ionized molecules to the detector while the applied electric field is maintained in the drift tube, thereby driving the additional ionized molecules toward the detector through the second ion gate to allow the detector to detect the additional batch of ionized molecules and records the second drift time.

6. The method of claim 1 wherein maintaining the first ion gate open to allow the drift tube being filled with additional ionized molecules includes maintaining the first ion gate open to allow the drift tube being filled with additional ionized molecules while the electric field is applied in the drift tube.

7. The method of claim 1 wherein:
the detector includes a mass spectrometer;
the first and second drift times individually include a set of mass-to-charge ratio data recorded by the mass spectrometer; and
deriving the final drift time includes deriving the final drift time by subtracting the second drift time from that of the first drift time and correlating each drift time of each ion to a mass-to-charge ratio recorded by the mass spectrometer.

8. The method of claim 1 wherein:
the detector includes a Faraday plate;
the first and second drift times individually include a set of current versus time data recorded by the Faraday plate; and
deriving the final drift time includes deriving the final drift time by subtracting the set of current versus time data of the second drift time from that of the first drift time.

9. The method of claim 1, further comprising:
introducing a drift gas into the drift tube to flow in a direction generally opposite of the drift direction; and
deriving a reduced mobility value of the sample as follows:

$$K_o = \frac{L^2}{Vt_d}\frac{P}{760}\frac{273.15}{T}$$

where L is a drift length that is a distance between the first and second ion gates, V is a voltage applied across L to generate the electric field, td is the final drift time across L, T is a temperature of a drift gas across L, and P is a pressure of the drift gas.

10. An ion mobility spectrometry system, comprising:
an ionization region configured to receive and ionize a sample into ionized molecules;
a detector configured to detect ionized molecules, the detector being spaced apart from the ionization region; and
a drift region in between and directly coupled to both the ionization region and the detector, the drift tube having:
a first ion gate proximate the ionization region;
a second ion gate proximate the detector, wherein the first and second ion gates are configured to alternately introduce a batch of ionized molecules toward the detector while the other is maintained open, thereby allowing the detector to measure a first drift time and a second drift time, respectively; and a controller operatively coupled to the first and second ion gates, the controller being configured to derive a reduced mobility value of the sample as follows:

$$K_o = \frac{L^2}{Vt_d}\frac{P}{760}\frac{273.15}{T}$$

where L is the drift length that is the distance between the first and second ion gates, V is a voltage applied across L to generate an electric field in the drift tube, $t_d$ is a drift time that is a difference between the first drift time measured when the first ion gate is pulsed while the second ion gate is open and the second drift time measured when the second ion gate is pulsed while the first ion gate is open, T is a temperature across L of a drift gas in the drift tube, and P is a pressure of the drift gas.

11. The ion mobility spectrometry system of claim 10 wherein the first and second ion gates individually include a Bradbury-Nielson or a Tyndall-Powell gate.

12. The ion mobility spectrometry system of claim 10 wherein:
the first ion gate is configured to open to introduce a batch of ionized molecules toward the detector while the second ion gate is maintained open during a first stage of operation; and
the second ion gate is configured to open to introduce another batch of ionized molecules toward the detector while the first ion gate is maintained open during a second stage of operation after the first stage of operation.

13. The ion mobility spectrometry system of claim 10 wherein:
the drift tube includes an electric field generator that is configured to generate an electric field in the drift tube when the first or second ion gate introduces the batch of ionized molecules toward the detector.

14. The ion mobility spectrometry system of claim 10 wherein:
the first ion gate is configured to open to introduce a batch of ionized molecules toward the detector while the second ion gate is maintained open during an initial stage of operation to collect data of the first drift time; and
the second ion gate is configured to open to introduce another batch of ionized molecules toward the detector while the first ion gate is maintained open during another stage of operation to collect data of the second drift time when the collected data of the first drift time is sufficient.

15. A method for performing ion mobility spectrometry in a drift tube having a first ion gate proximate an ionization region and a second ion gate proximate a detector, the first and second ion gates being arranged along a drift direction of the drift tube, the method comprising:
receiving and ionizing, using the ionization region, a sample into ionized molecules;
applying control signals to the first and second ion gates to cause the first and second ion gates to alternately introduce a batch of the ionized molecules from the ionization region toward the detector with an applied electric field in the drift tube while the other one of the first or second ion gate is maintained open;
detecting and obtaining, using the detector, first and second drift times of the ionized molecules corresponding to (i) when the second ion gate is maintained open and (ii) when the first ion gate is maintained open; and deriving a final drift time corresponding to a drift length that is a distance between the first and second ion gates by subtracting the second drift time from the first drift times.

16. The method of claim 15 wherein applying the control signals includes applying the control signals to:

pulsing open the first ion gate to introduce a batch of ionized molecules toward the detector while the second ion gate is maintained open during a first stage of operation; and pulsing the second ion gate to introduce another batch of ionized molecules toward the detector while the first ion gate is maintained open during a second stage of operation after the first stage of operation.

17. The method of claim 15 wherein applying the control signals includes applying the control signals to:

pulsing open the first ion gate to introduce a batch of ionized molecules toward the detector while the second ion gate is maintained open to collect data of a first drift time; and pulsing the second ion gate to introduce another batch of ionized molecules toward the detector while the first ion gate is maintained open to collect data of a second drift time when the collected data of the first drift time is sufficient.

18. The method of claim 15 wherein applying the control signals includes applying the control signals to:

maintain the first ion gate open to fill the drift tube with the ionized molecules; and subsequently, open the second ion gate to introduce another batch of ionized molecules toward the detector under the applied electric field while the first ion gate is maintained open during a second stage of operation after the first stage of operation.

19. The method of claim 15, further comprising:

introducing a drift gas into the drift tube to flow in a direction generally opposite of the drift direction; and deriving a reduced mobility value of the sample as follows:

$$K_o = \frac{L^2}{Vt_d} \frac{P}{760} \frac{273.15}{T}$$

where L is a drift length that is a distance between the first and second ion gates, V is a voltage applied across L to generate the electric field, td is the final drift time across L, T is a temperature across L of a drift gas, and P is a pressure of the drift gas.

* * * * *